(12) United States Patent
Hamada et al.

(10) Patent No.: US 10,768,090 B2
(45) Date of Patent: Sep. 8, 2020

(54) PARTICLE COUNTING APPARATUS

(71) Applicant: HORIBA, Ltd., Kyoto-shi, Kyoto (JP)

(72) Inventors: Motoaki Hamada, Kyoto (JP);
Kazumasa Takemoto, Kyoto (JP); Yoji Kawanami, Kyoto (JP)

(73) Assignee: HORIBA, Ltd., Kyoto-shi, Kyoto (JP)

( * ) Notice: Subject to any disclaimer, the term of this patent is extended or adjusted under 35 U.S.C. 154(b) by 0 days.

(21) Appl. No.: 16/470,097

(22) PCT Filed: Sep. 12, 2017

(86) PCT No.: PCT/JP2017/032824
§ 371 (c)(1),
(2) Date: Jun. 14, 2019

(87) PCT Pub. No.: WO2018/110007
PCT Pub. Date: Jun. 21, 2018

(65) Prior Publication Data
US 2019/0317007 A1    Oct. 17, 2019

(30) Foreign Application Priority Data
Dec. 15, 2016  (JP) .................... 2016-243852

(51) Int. Cl.
*G01N 15/12* (2006.01)
*G01N 33/487* (2006.01)
(Continued)

(52) U.S. Cl.
CPC ....... *G01N 15/12* (2013.01); *G01N 33/48707* (2013.01); *G01N 33/49* (2013.01);
(Continued)

(58) Field of Classification Search
CPC ...... G01R 33/09; G01R 33/093; G01R 33/07; H01L 2224/48247
(Continued)

(56) References Cited

U.S. PATENT DOCUMENTS 4,157,499 A    6/1979  Kacerek
6,106,778 A    8/2000  Oku et al.
(Continued)

FOREIGN PATENT DOCUMENTS

JP    S55008752 A    1/1980
JP    S55143431 A    11/1980
(Continued)

OTHER PUBLICATIONS

ISA European Patent Office, International Search Report Issued in Application No. PCT/JP2017/032824, dated Dec. 19, 2017, WIPO, 9 pages.

*Primary Examiner* — Giovanni Astacio-Oquendo
(74) *Attorney, Agent, or Firm* — Alleman Hall Creasman & Tuttle LLP (57) ABSTRACT

An outside opening of each aperture of a plurality of counting chambers for performing particle counting based on the electric resistance method is connected to suction pump through a confluent piping. Liquid supplying part supplies an additional liquid to the counting chamber side after completion of counting of counting chamber, so that the liquid level of sample liquid of counting chamber will not descend to aperture or a predetermined liquid level.

4 Claims, 8 Drawing Sheets

(51) Int. Cl.
 *G01N 33/49* (2006.01)
 *G01N 15/10* (2006.01)
(52) U.S. Cl.
 CPC .............. *G01N 2015/1062* (2013.01); *G01N 2015/1254* (2013.01)
(58) Field of Classification Search
 USPC .................. 324/701, 760.01, 200, 244, 252
 See application file for complete search history.

(56) References Cited

U.S. PATENT DOCUMENTS

| | | | |
|---|---|---|---|
| 7,719,027 B2* | 5/2010 | Chen | H01L 23/3107 257/177 |
| 2004/0169262 A1* | 9/2004 | Oliver | H01L 23/49575 257/676 |
| 2005/0190624 A1* | 9/2005 | Kasai | G11C 7/10 365/222 |
| 2014/0341779 A1 | 11/2014 | Takemoto | |

FOREIGN PATENT DOCUMENTS

| | | |
|---|---|---|
| JP | S56077743 A | 6/1981 |
| JP | 09089908 A | 4/1997 |
| JP | 3477352 B2 | 9/2003 |
| JP | 2005091098 A | 4/2005 |
| JP | 2014224754 A | 12/2014 |
| WO | 0111338 A1 | 2/2001 |
| WO | 03104770 A2 | 12/2003 |

\* cited by examiner

PARTICLE COUNTING APPARATUS

TECHNICAL FIELD

The present invention relates to a particle counting apparatus that counts particles in a sample liquid based on the electric resistance method.

BACKGROUND ART

Figure 7A:
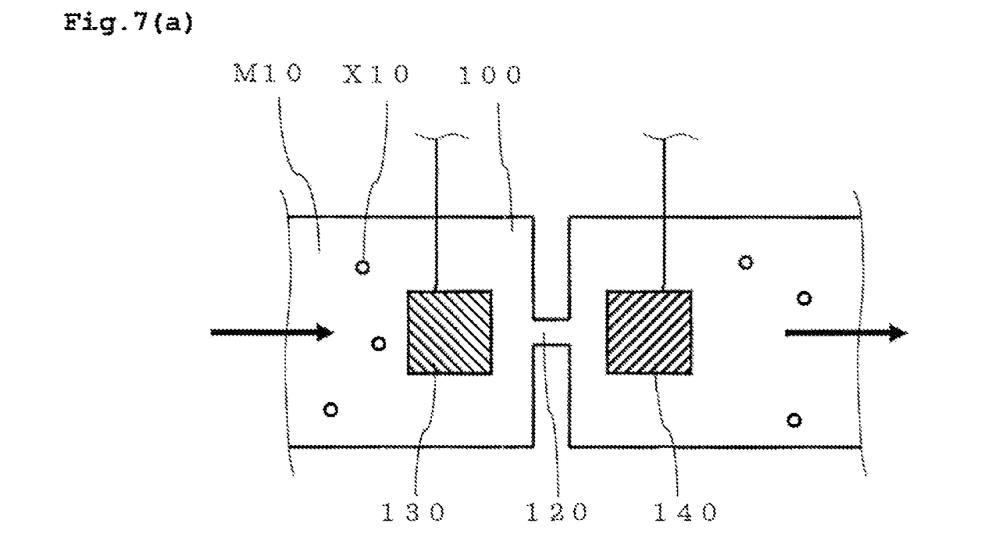
FIGS. 7(a) and 7(b) show the principle of particle counting based on the electric resistance method.
Figure 7B:
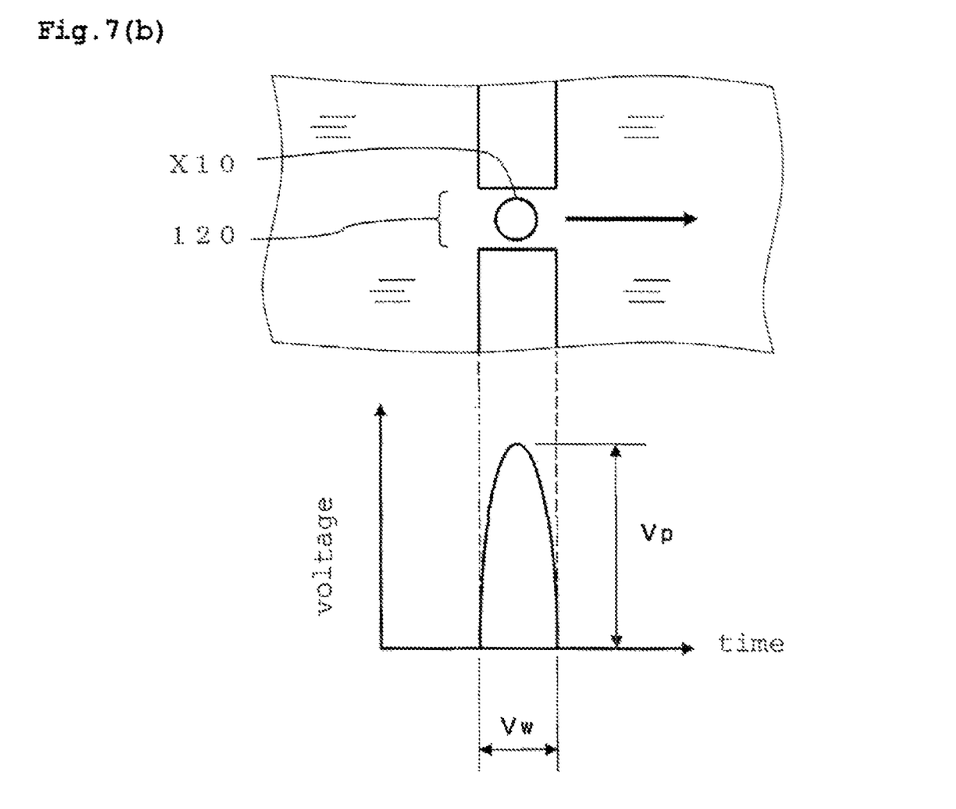

As a method for counting particles in a sample liquid, the electric resistance method (also referred to as an impedance method) is known (patent document 1 and the like). In particle counting based on the electric resistance method, as shown in FIG. 7(a), an aperture (narrow part) 120 is provided on a flow path 100, and a pair of electrodes 130, 140 are provided sandwiching the aperture 120 in the flow direction. When particles X10 in a sample liquid M10 pass through the aperture 120, the electric resistance (or impedance) between electrodes 130, 140 changes in a pulse-shape. Therefore, for example, when a voltage is applied between the electrodes using a constant-current power supply (not shown), as shown in FIG. 7(b), the applied voltage also changes as a pulse voltage. The number of particles can be known by counting and/or measuring the number and characteristics of the pulse voltages in an arithmetic part (not shown) or the like. It is also possible to know the volume of the particle from the height Vp and width Vw of the pulse voltage.

Figure 8:
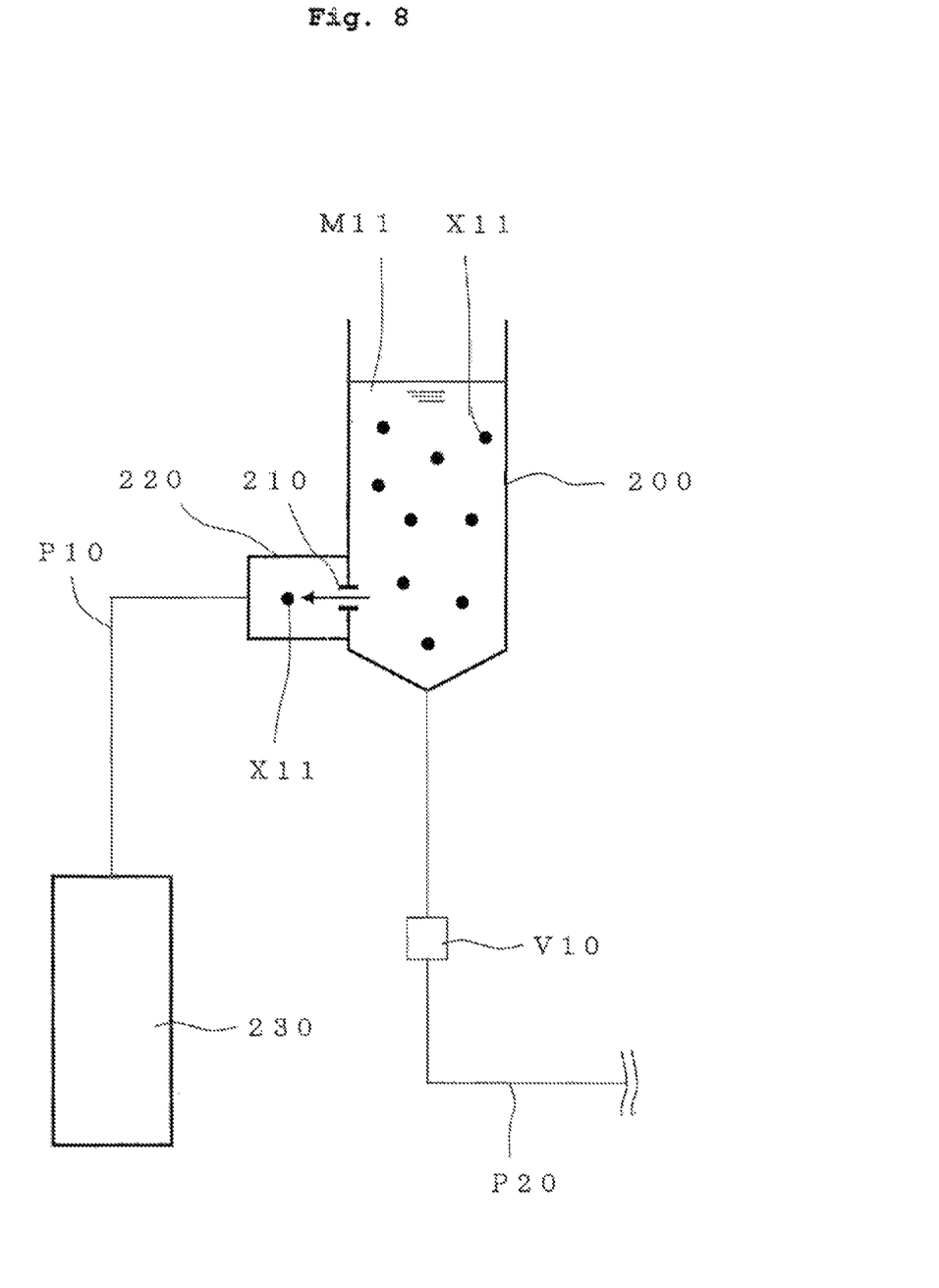
FIG. 8 is a block diagram showing the configuration of the main part of a conventional counting apparatus for counting blood cells based on the electric resistance method.

For example, in conventional counting apparatuses that count blood cells based on the electric resistance method, as shown in FIG. 8, an aperture 210 is provided in a lower part of the side wall of a counting chamber 200 to contain a sample liquid. Through the aperture, the counting chamber is in communication with a small chamber 220 adjacent to the outer side. An electrode for the electric resistance method is provided in each of the counting chamber and the small chamber (electrode is not shown). The small chamber 220 is communicated with a suction pump 230 through a piping P10. A diluted sample liquid (blood) is injected into the counting chamber 200 as a sample liquid M11. When the suction pump 230 sucks the sample liquid M11, blood cells X11 in the sample liquid in the counting chamber pass through the aperture one by one as shown with an arrow, and blood cell counting based on the electric resistance method is performed as explained above by reference to FIGS. 7(a) and 7(b).

DOCUMENT LIST

Patent Document patent document 1: JP-A-2005-091098

SUMMARY OF THE INVENTION

Problems to be Solved by the Invention

Particle counting apparatuses are sometimes provided with a plurality of counting chambers to enable individual counting of plural kinds of particles. For example, blood cell counting apparatuses are sometimes provided with a red blood cell counting chamber and a white blood cell counting chamber to respectively count red blood cells and white blood cells. In the red blood cell counting chamber, platelets may also be counted. These counting chambers are each provided with an aperture similar to the embodiment of FIG. 8 and an outlet side of the aperture is connected to the suction pump.

Figure 1:
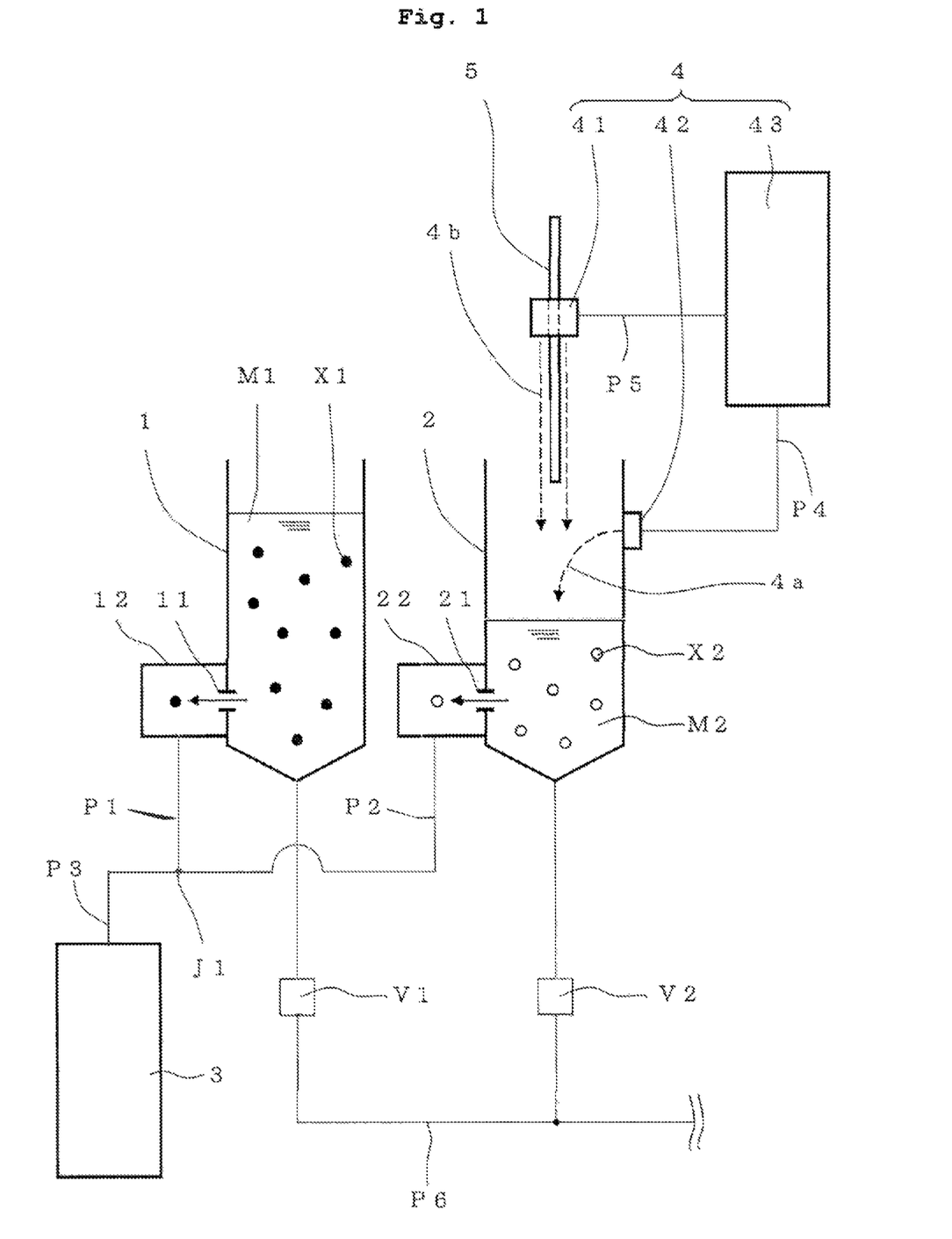
FIG. 1 is a block diagram illustrating the configuration of the main part of the particle counting apparatus of the present invention. In this Figure, piping is shown with thin lines (same in other Figures).

The present inventors conceived a constitutional idea of sucking a sample liquid in each counting chamber by one common suction pump as shown in FIG. 1 rather than providing an individual suction pump when a plurality of counting chambers are present.

However, in a blood cell counting apparatus, for example, the amount of a sample liquid in the white blood cell counting chamber is sometimes is remarkably smaller than the amount of a sample liquid in the red blood cell counting chamber due to difference in the dilution ratio. Furthermore, extension of the counting time in the red blood cell counting chamber more than usual may become necessary depending on the sample fluid.

Therefore, it was newly found that when the sample liquid in the red blood cell counting chamber and the sample liquid in the white blood cell counting chamber are actually sucked by one suction pump, counting in the white blood cell counting chamber completes first, and a liquid level of the sample liquid in the white blood cell counting chamber descends to the aperture first, and the air is sucked into the aperture, which in turn prevents sucking of the sample liquid in the red blood cell counting chamber by the suction pump.

This problem similarly occurs not only when counting blood cells but also when counting particles in other sample liquid.

The problem of the present invention is to solve the above-mentioned problem and provide a particle counting apparatus having a configuration in which a sample liquid in each of a plurality of counting chambers for particle counting based on the electric resistance method is sucked by a common suction pump, and capable of preferably completing the particle counting in any counting chamber.

Means of Solving the Problems

Accordingly, the main configuration of the present invention is as follows.

[1] A particle counting apparatus for counting particles in a sample liquid, comprising
a plurality of counting chambers each provided with an aperture and a pair of electrodes for counting particles based on the electric resistance method,
a suction pump, and
a liquid supplying part for supplying a liquid to one or more predetermined counting chambers,
wherein
the aperture of each of the aforementioned plurality of counting chambers has an outside opening connected to the aforementioned suction pump through a confluent piping, and
the liquid supplying part supplies a liquid to said one or more predetermined counting chambers or to a flow path on the predetermined counting chamber side than a confluent part in the aforementioned confluent piping, after completion of counting in said one or more predetermined counting chambers, such that a liquid level of the sample liquid in said one or more predetermined counting chambers would not descend to the aperture or to a predetermined liquid level above the aperture.

[2] The particle counting apparatus according to the aforementioned [1], wherein
the above-mentioned plurality of counting chambers are cylindrically-shaped containers with a same inner diameter, and a liquid level of the sample liquid in a counting chamber in which the counting is completed last is higher than the liquid level of the sample liquid in the above-mentioned one or more predetermined counting chambers at the time point when the sample liquid has been injected into each of the plurality of counting chambers.

[3] The particle counting apparatus according to the aforementioned [1] or [2], wherein
the above-mentioned plurality of counting chambers comprise a red blood cell counting chamber and a white blood cell counting chamber,
a counting chamber in which the counting is completed last is the red blood cell counting chamber, and
the above-mentioned one or more predetermined counting chambers are white blood cell counting chambers.

[4] The particle counting apparatus according to any of the aforementioned [1] to [3],
wherein
the liquid supplied by the above-mentioned liquid supplying part is a diluent, and
the above-mentioned liquid supplying part comprises one or both of a diluent supplying device of the following (I) and a sampling-nozzle washer of the following (II):
(I) a diluent supplying device comprising a diluent supplying source, a diluent supply port provided in the above-mentioned one or more predetermined counting chambers, and a diluent supplying piping connecting the diluent supplying source and the diluent supply port
(II) a sampling nozzle washer comprising a diluent supplying source, a diluent outlet part accompanying a sampling nozzle provided in the particle counting apparatus, and a diluent supplying piping connecting the diluent supplying source and the diluent outlet part, wherein an outer surface of the sampling nozzle is washed while allowing the diluent to flow out on and drop from the outer surface.

Effect of the Invention

In the present invention, a liquid supplying part is provided. Therefore, despite the configuration in which each sample liquid in a plurality of counting chambers is simultaneously sucked through each aperture by a common suction pump, it is possible to prevent problems such as air being sucked into the aperture in a counting chamber containing a small amount of the sample liquid, and the suction pump can continue to preferably suck the sample liquid until the particle counting is complete even in the counting chamber in which the counting is completed last.

DESCRIPTION OF EMBODIMENTS

In the present specification, the "amount" in the amount of the sample liquid, the supply amount of the additional liquid, the dispensed amount of the sample liquid, predetermined amount, known amount and the like means volume.

The particle counting may be simple counting of the number of particles, or may also include determination of particles having what volume are present in what number in addition to the simple counting.

The particle counting apparatus of the present invention is described in detail in the following by illustrating examples.

FIG. 1 is a block diagram illustrating the configuration of the main part of the particle counting apparatus. As shown in FIG. 1, the particle counting apparatus is an apparatus for counting the particles in a sample liquid, and has a plurality of counting chambers 1, 2, a suction pump 3, and a liquid supplying part 4 that supplies the liquid to the counting chambers 1, 2. In this example, for explanation, the number of a plurality of counting chambers is 2. However, the number of the counting chambers is not particularly limited and other counting chamber(s) may also be present. In this example, red blood cell and white blood cell are used as examples of the particles in a sample liquid, and a blood cell counting apparatus is used as an example of the apparatus. However, the particles to be counted are not limited to blood cells, and the apparatus may be other general particle counting apparatus. The two counting chambers 1, 2 used in this example are respectively a red blood cell counting chamber 1 constituted to count red blood cells and a white cell counting chamber 2 constituted to count white blood cells. The red blood cell counting chamber may also count platelets. In the following, the red blood cell counting chamber is also abbreviated as RBC (Red Blood Cell) chamber and the white blood cell counting chamber is also abbreviated as WBC (White Blood Cell) chamber.

The aforementioned plurality of counting chambers (RBC chamber 1 and WBC chamber 2 in this example) are respectively provided with an aperture and an electrode pair, and have a configuration enabling particle counting based on the electric resistance method. More specifically, as shown in FIG. 1, RBC chamber 1 is provided with an aperture 11 and a pair of electrodes, and WBC chamber 2 is similarly provided with an aperture 21 and a pair of electrodes. In FIG. 1, the electrodes are omitted to clearly show the drawing.

A suction pump 3 is provided to the particle counting apparatus. The suction pump 3 is a common pump for sucking sample liquids M1, M2 each injected into the plurality of counting chambers (RBC chamber 1, WBC chamber 2 in this example) respectively through apertures 11, 21. Outside opening apertures 11, 21 are each connected to the suction pump 3 through confluent pipings P1-P3. More specifically, Pipings P1, P2 are connected to the outside opening apertures 11, 21 of the counting chambers 1, 2, these pipings P1, P2 join the piping P3 at a confluence part J1, and the piping P3 is connected to the suction pump 3. By this confluent piping, the sample liquids contained in the plurality of counting chambers 1, 2 can be simultaneously sucked by a single common suction pump 3.

The liquid supplying part 4 supplies a liquid (e.g., diluent 4a or 4b in the example of FIG. 1) to a predetermined counting chamber or to a flow path on the predetermined counting chamber side than a confluent part J1 in the aforementioned confluent piping, after completion of the counting of the predetermined counting chamber, such that the liquid level of the sample liquid in one or more counting chambers would not descend to the aperture or to a predetermined liquid level above the aperture. In the following, this liquid is referred to as an additional liquid and distinguished from other liquids. The number of the predetermined counting chambers to which an additional liquid is to be supplied is one or more. In the following explanation, the predetermined counting chamber to which an additional liquid is to be supplied is simply referred to as "the predetermined counting chamber". All counting chambers for performing particle counting based on the electric resistance method which are provided in plurality in the apparatus are simply referred to as "all counting chambers".

The predetermined counting chamber is exemplified by a counting chamber which, when the liquid supplying part 4 does not supply a liquid, completes counting before completion of counting of a counting chamber that completes counting last in all counting chambers and shows the liquid level of the sample liquid having descended to the aperture.

In this example, the predetermined counting chamber is a WBC chamber 2, the counting chamber that completes counting last in all counting chambers 1, 2 is the RBC chamber 1. This example shows an embodiment in which the liquid supplying part 4 supplies a liquid in the predetermined counting chamber. A preferable embodiment of the confluent piping and an embodiment in which the liquid supplying part 4 supplies a liquid in a flow path on the predetermined counting chamber side than the confluent part J1 in the confluent piping are described later.

Generally, the initial amount of the sample liquid (amount of liquid at the time of start of counting when sample liquid is diluted) to be supplied to WBC chamber 2 as the predetermined counting chamber is sometimes remarkably smaller than the initial amount of the sample liquid in the RBC chamber 1 due to the difference in the dilution ratio. Furthermore, when the measurement precision and reproducibility need to be improved more and the like, extension of the counting time in the RBC chamber more than usual may become necessary depending on the sample. Therefore, when the liquid supplying part 4 did not supply the additional liquid into the WBC chamber 2, the WBC chamber 2 completes counting before the completion of counting of the RBC chamber 1 and the liquid level of the sample liquid descends to the aperture, which in turn may cause a trouble of the air being sucked into the aperture to adversely influence sucking of the sample liquid in RBC chamber 1.

In contrast, in the present invention, since the liquid supplying part 4 can supply an additional liquid into the WBC chamber 2 as the predetermined counting chamber after completion of counting of the WBC chamber 2, the liquid level of the sample liquid in the WBC chamber 2 does not descend to the aperture even when the suction pump 3 continues to suck each sample liquid in the RBC chamber 1 and the WBC chamber 2, whereby sucking of the air into the aperture no longer occurs. A similar effect can also be obtained by supplying an additional liquid into the flow path on the predetermined counting chamber side than the confluence part J1 in the confluent piping. When the additional liquid is supplied into the flow path on the predetermined counting chamber side than the confluence part J1 in the confluent piping, sucking itself of the sample liquid M2 through the aperture 21 is prevented, whereby descending of the liquid level of the sample liquid M2 to the aperture 21 is prevented. Thus, even when the number of the suction pump 3 is one, the sample liquid M1 can be preferably sucked continuously from the RBC chamber 1 until completion of counting of the RBC chamber 1 that completes the counting lastly. On this occasion, a mixture of the remaining sample liquid M2 and the supplied additional liquid is also simultaneously sucked from the WBC chamber 2.

In the following explanation, supply of an additional liquid into the predetermined counting chamber means not only supply of an additional liquid into the predetermined counting chamber but also alternately means supply of an additional liquid into a flow path on the predetermined counting chamber side than the confluence part J1 in the confluent piping.

Figure 2:
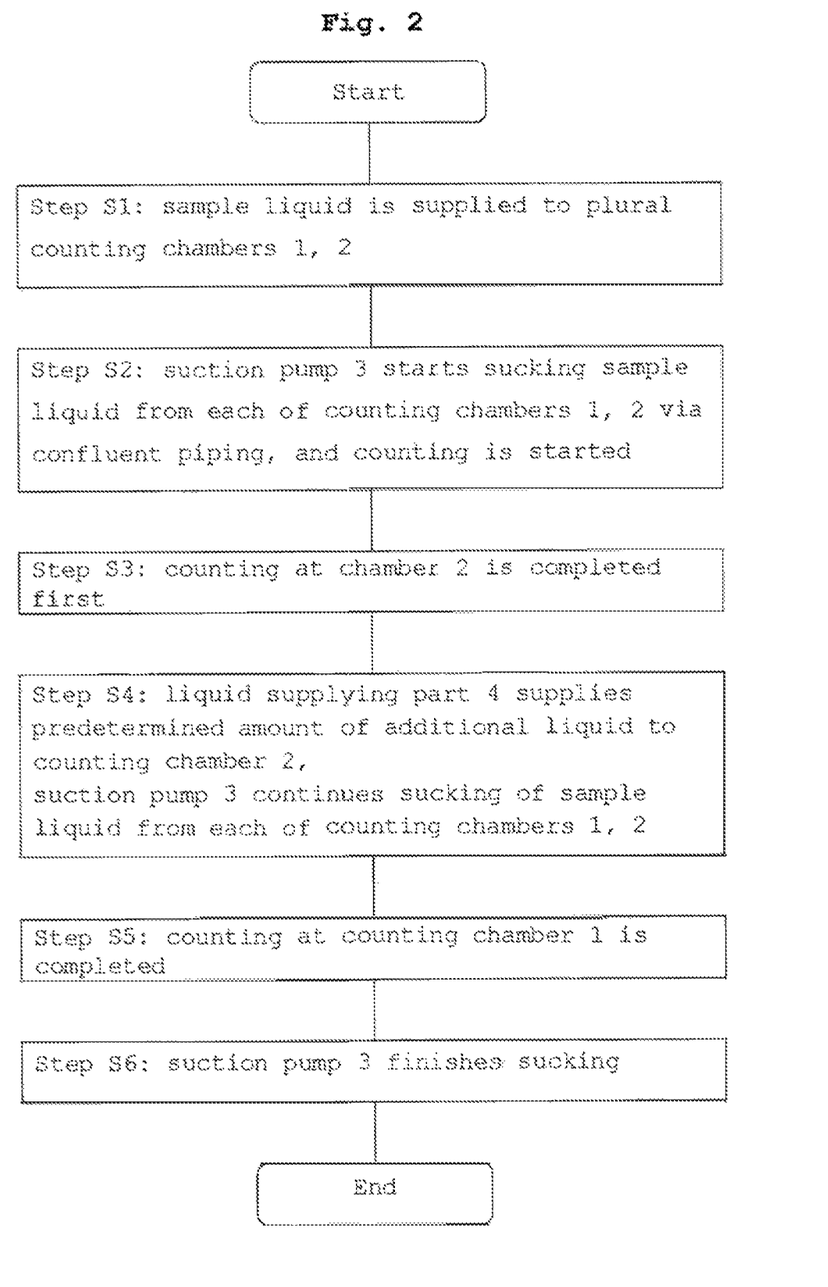
FIG. 2 is a flowchart showing an example of the action of the main part in the particle counting apparatus of the present invention.

FIG. 2 is a flowchart showing the action of the main part in the particle counting apparatus. In the flowchart in this Figure, the action of the configuration example of FIG. 1 is shown to clearly show the action of each part, wherein the number of counting chambers is two. While examples in which counting of the counting chamber 2 completes first are shown, they do not limit the present invention.

As shown in the flowchart in this Figure, in the particle counting apparatus, when the action of each part for counting particles (blood cells) is started, sample liquids M1, M2 are first supplied to all counting chambers 1, 2 in step S1.

Then, in step S2, the suction pump 3 starts sucking of the sample liquid from each of the counting chambers 1, 2 through confluent pipings P1-P3, whereby particle counting is started.

Then, in step S3, particle counting of the counting chamber 2 is completed first.

Then, in step S4, the liquid supplying part 4 supplies a predetermined amount of the additional liquid to the counting chamber 2. Meanwhile, the suction pump 3 continues to suck the sample liquid from each of the counting chambers 1, 2.

Then, in step S5, particle counting of the counting chamber 1 is completed.

Then, in step S6, the suction pump 3 finishes sucking, and the action of each part for particle counting in the particle counting apparatus is completed.

The configuration of each part of the particle counting apparatus and modified embodiments thereof are explained in detail below.

In the example of FIG. 1, the number of the counting chambers is two but the number of the counting chambers may be three or more. For example, a case including a counting chamber (I) in which the counting is completed first, then a counting chamber (II) in which the counting is completed next and a counting chamber (III) in which the counting is completed last is explained.

In the counting chamber (I), when the liquid supplying part 4 does not supply an additional liquid, counting is completed before completion of the counting of the counting chamber (III) and the liquid level of the sample liquid descends to the aperture or a predetermined liquid level. In the counting chamber (II), when the liquid supplying part 4 does not supply an additional liquid, counting is completed before completion of the counting of the counting chamber (III) but the liquid level of the sample liquid does not descend to the aperture or a predetermined liquid level.

In such a case, the liquid supplying part 4 supplies an additional liquid to counting chamber (I) after completion of the counting, and prevents the liquid level of the sample liquid from descending to the aperture or predetermined liquid level. On the other hand, supply of the additional liquid to the counting chamber (II) is not necessary. This is because the liquid level of the sample liquid in counting chamber (II) does not descend to the aperture until completion of the counting of counting chamber (III), and the air is not sucked into the aperture.

As described above, even when the number of the counting chambers is 3 or more, a counting chamber to which the additional liquid is to be supplied can be appropriately selected. Even when the liquid level of the sample liquid descends to the aperture or a predetermined liquid level in a plurality of counting chambers (I) during counting of the above-mentioned counting chamber (III), an additional liquid is appropriately supplied to such counting chambers.

Supply Target, Supply Time, Supply Amount of Additional Liquid

The counting chamber to which the additional liquid is to be supplied, supply time of the additional liquid, and supply amount of the additional liquid can be previously set as follows and are known.

(i) The initial amount of the sample liquid to be supplied into each of all counting chambers (liquid amount at the start of counting after dilution of the sample liquid) is generally a known amount set in advance. For example, in case of blood cell counting, only a predetermined amount of the original sample liquid (whole blood and the like) is dispensed to each counting chamber, only a predetermined amount of a reagent is added for counting of each counting chamber, a predetermined amount of a diluent is added, and a predetermined amount of a sample liquid is prepared for each counting chamber. Alternatively, a part (predetermined amount) of a sample liquid diluted to a predetermined value in a counting chamber may be divided for other counting chamber and a predetermined amount of a diluent may be further added. Thus, the initial amount of the sample liquid in each counting chamber is generally a known amount set in advance.

(ii) The inner diameter of each counting chamber, position of each aperture, pore size of each aperture and initial liquid level of the sample liquid are also known, and the sucking amount per second of one suction pump, the flow rate per second of each sample liquid that passes the aperture of each counting chamber, and the descending velocity per second of the liquid level of the sample liquid in each counting chamber are also set in advance or as calculated and known. The total flow rate per second of each sample liquid that passes the aperture of each counting chamber is equal to the sucking amount per second of the suction pump.

(iii) Therefore, among all counting chambers, which is the counting chamber in which the counting is completed last (hereinafter accorded with symbol C1) and when the counting completion time of counting chamber C1 is (hereinafter accorded with symbol T1) are also set in advance or as calculated and known. The counting completion time T1 of counting chamber C1 is preferably before the time when the liquid level of the sample liquid descends to the aperture or a predetermined liquid level in counting chamber C1. The initial amount of the sample liquid in counting chamber C1 is preferably a predetermined amount so that the liquid level of the sample liquid will not descend to the aperture or a predetermined liquid level before the counting completion time T1.

(iv) Similar to the aforementioned counting chamber C1, which is the counting chamber to which the additional liquid is to be supplied (hereinafter accorded with symbol C2), when the additional liquid is to be supplied to counting chamber C2 (hereinafter accorded with symbol T2), and further, the amount of the additional liquid to be supplied to counting chamber C2 may be set in advance or as calculated and known. A necessary amount of the additional liquid to be supplied to counting chamber C2 may be added once, or may be continuously supplied until counting completion time T1 of the above-mentioned counting chamber C1 at a flow rate that does not descend the liquid level of the sample liquid in consideration of the flow rate of the sample liquid that flows out from the aperture. The flow rate of the sample liquid that flows out from the aperture can be determined in advance according to the sucking amount per second of the suction pump, number of the counting chambers, pore size of each aperture and the like, and is an important amount for particle counting.

The time T2 at which the additional liquid is supplied to the counting chamber C2 is preferably after completion of the counting of counting chamber C2. This is because supply of the additional liquid before completion of the counting of counting chamber C2 influences the results of the particle counting of counting chamber C2.

(v) From (i)-(iv) above, liquid supplying part 4 supplies a predetermined amount of an additional liquid to predetermined counting chamber C2 at predetermined time T2 after start of counting in each counting chamber, and can prevent the liquid level of the sample liquid from descending to the aperture or predetermined liquid level in counting chamber C2. The action of each part above, height of the liquid level and the like may be controlled by a control part. The control part is described below.

The above-mentioned predetermined liquid level to be set above the aperture is a height of a liquid surface that is preferably set in advance for safety. The predetermined liquid level may be set for each counting chamber. The predetermined liquid level can be calculated from the inner diameter of each counting chamber and the descend velocity of the liquid level of the sample liquid, and can be stored by the below-mentioned control part in a manner utilizable for the control part. A specific value of the predetermined liquid level can be determined according to the counting chamber and in consideration of the safety, and is not particularly limited and, for example, a position above (e.g., about several mm above) the uppermost edge of the opening of the aperture can be mentioned.

In each counting chamber, changes such as extension or shortening of the counting time may be added depending on the result of counting. For example, as mentioned below, the control part is preferably configured to determine whether or not the counting result for each counting chamber satisfies the determination condition set in advance, and performs counting for an extended time in a counting chamber in which the counting result does not satisfy the determination condition. The conditions set in advance include, for example, the case where the counting result of blood cells or platelets is not within a predetermined range. More specific examples include cases where the platelet count result is less than 100000 platelets/µL and the like. Such extension of the counting time is preferable because it eliminates the labor for retesting.

However, the amount of the sample liquid to be supplied to each counting chamber is a predetermined amount. When the counting time of a certain counting chamber (e.g., RBC chamber 1 in FIG. 1) is extended, counting may be completed first and the liquid level may descend to a predetermined liquid level in other counting chamber (e.g., WBC chamber 2 in FIG. 1).

In contrast, even when such change of the counting time is made in the present invention, due to the configuration in which liquid supplying part 4 supplies an additional liquid to other counting chamber in which the liquid level descends to a predetermined liquid level, the counting time in the object counting chamber can be extended without a trouble of the liquid level having descended to the aperture of the other counting chamber.

Detection of Counting Chamber to Which Additional Liquid is to be Supplied

Even when the counting chamber to which an additional liquid is to be supplied is not known, a liquid level detection sensor and the like may be provided at the detecting position set above the aperture of each counting chamber, and the counting chamber to which the additional liquid is to be supplied may be detected thereby. In such embodiment, a control configuration in which the liquid level detection sensor of a certain counting chamber detects the liquid level of the sample liquid, the liquid supplying part 4 acts according to the detection signal, and a predetermined amount of an additional liquid is supplied to the counting chamber can be mentioned.

Configuration for Practicing Electric Resistance Method

In the example shown in FIG. 1, as a preferable embodiment, small chambers 12, 22 are provided on the outer side of the aperture of respective counting chambers 1, 2. The aperture 11 connects counting chamber 1 and small chamber 12, and aperture 21 connects counting chamber 2 and small chamber 22. By providing a small chamber on the outer side of the opening aperture, one of a pair of electrodes is easily provided in a flow path on the outer side of the counting chamber. In addition, the small chamber serves as a pipe joint to facilitate connection of pipings P1 and P2 to the suction pump. Also, the small chamber suppresses turbulence of the flow in the aperture, and particle counting based on the electric resistance method can be performed more accurately.

The inner diameter of the aperture provided to each counting chamber, the shape and volume of the small chamber on the outer side of the aperture can be determined according to the size of the particles to be counted, and reference can be made to the configuration of a conventionally-known counting apparatus for counting particles based on the electric resistance method. Generally, the inner diameter of the aperture of RBC chamber 2 is smaller than the inner diameter of the aperture of WBC chamber 2.

For the electrode pair for counting particles based on the electric resistance method, an electrode pair provided in a conventionally-known counting chamber based on the electric resistance method can be referred to, such as FIGS. 7(a) and 7(b) and the like. In the example of FIG. 1, one of the electrodes is set in the counting chamber and the other electrode is set in the small chamber. Each electrode is connected to the below-mentioned control part, and particle counting based on the electric resistance method can be executed.

Confluent Piping

As the confluent piping, a piping which can suck the sample liquid of all counting chambers by one suction pump is utilizable. In the example of FIG. 1, piping P1 is connected to small chamber 12 on the outer side of aperture 11 of RBC chamber 1, piping P2 is connected to small chamber 22 on the outer side of aperture 21 of RBC chamber 2, these pipings P1, P2 are joined together at confluence part J1 to be piping P3, and piping P3 is connected to suction pump 3. In such embodiment, it is preferable to use a pipe joint capable of applying a sucking force evenly to the piping P1 and piping P2 for joining at confluence part J1.

Figure 3:
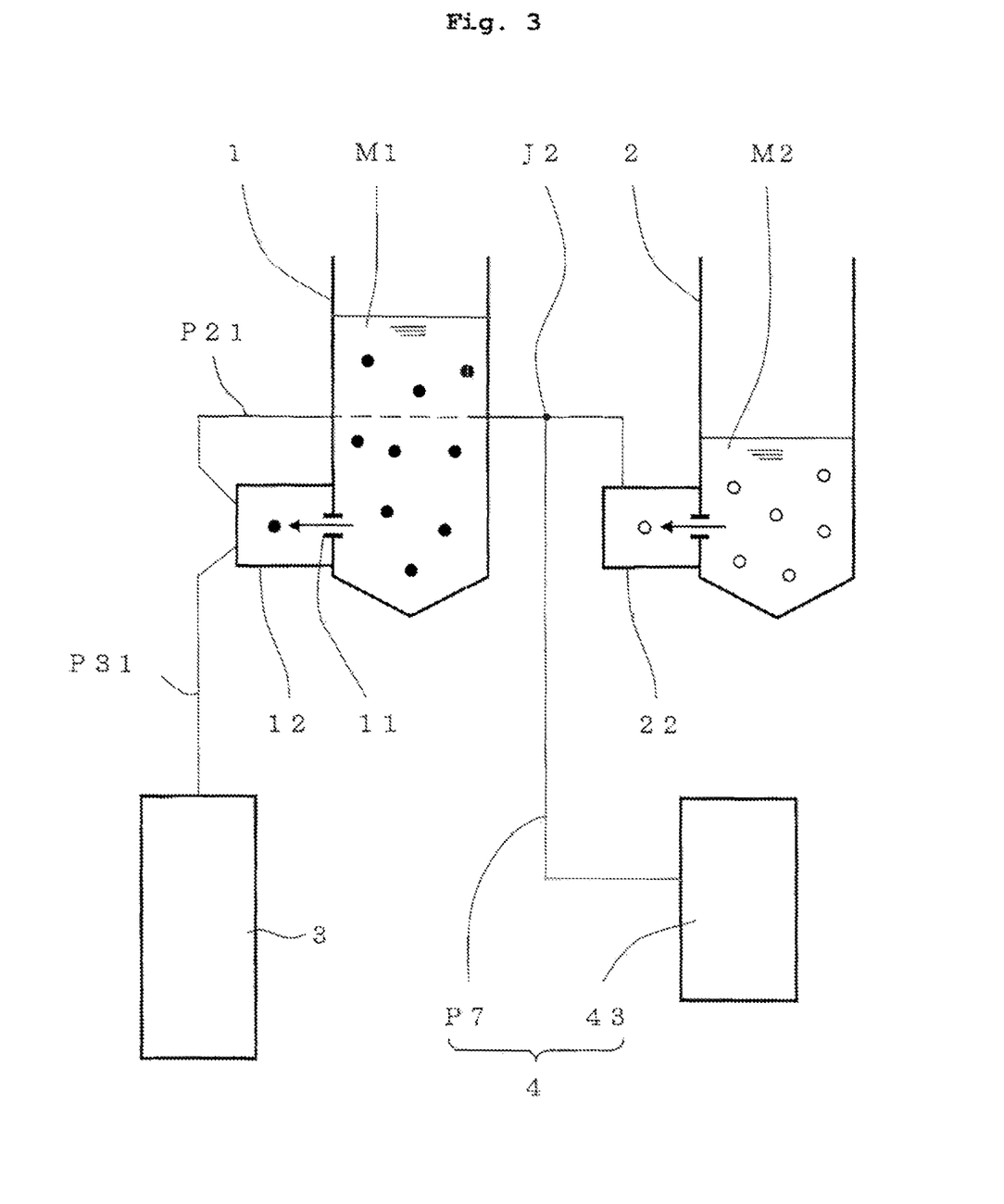
FIG. 3 is a block diagram showing an example of a preferable embodiment of the confluent piping shown in FIG. 1. In this Figure, the same symbol is used for the same part as in FIG. 1, and illustration of parts other than those related to the confluent piping is omitted. The part in a dashed line in piping P21 shows that the piping P21 passes the outer side of the counting chamber 1.

FIG. 3 is a block diagram showing an example of a preferable embodiment of the confluent piping shown in FIG. 1. In the embodiment of this Figure, piping P21 is connected to small chamber 22 of WBC chamber 2, the piping P21 is connected to small chamber 12 of RBC chamber 1, whereby small chamber 12 serves as a confluence part. Piping P31 is connected to small chamber 12, piping P31 is connected to suction pump 3, and two sample liquids M1, M2 are joined together in the inside of small chamber 12 and sucked by suction pump 3.

The connecting configuration of the piping in the case of using the small chamber as the confluence part is not particularly limited, and the embodiment illustrated in FIG. 3 shows a preferred connection configuration. In the embodiment of FIG. 3, piping P21 is connected to the small chamber 12 in an inclined manner such that the liquid flow that flows into small chamber 12 from piping P21 advances toward the inlet of piping P31. On the other hand, piping P31 is connected to the small chamber 12 in an inclined manner such that it receives the liquid that flows into small chamber 12 from piping P21 more smoothly. By the connection of piping P21 on the inlet side and piping P31 on the outlet side to small chamber 12, a rectification effect on the flow of sample liquid M1 that comes out from aperture 11 can be obtained.

Suction Pump

Suction pumps capable of sucking the sample liquid of each counting chamber through the aperture with the accuracy necessary for counting are utilizable. Such suction pump includes a quantitative discharging device (syringe) having a cylinder and a piston.

The quantitative discharging device is a device in which the piston can be driven according to the control by the control part described later and can suck the sample liquid into the cylinder through the confluent piping. It is preferable that an electromagnetic valve for sucking the sample liquid from the confluent piping and discharging the sucked sample liquid to the waste liquid piping be provided in the quantitative discharging device. For the detailed structure inside the quantitative discharging device, the electromagnetic valve for switching the piping path attached thereto or closing the piping path, the piping for waste liquid, and the like, the known art may be referred to and they are not shown in the present specification.

Embodiment of Liquid Supplying Part

As liquid supplying part 4, an apparatus constituted to supply the additional liquid to the predetermined counting chamber described above can be utilized. The liquid supplying part 4 may be a device newly added to supply the additional liquid to a conventional particle counting apparatus. It is a preferred embodiment to use the diluent supplying device already attached to the particle counting apparatus as the liquid supplying part 4. In other words, it is a preferable embodiment to modify the content of control by the control part described later and to operate the existing diluent supplying device as the liquid supply part 4. The counting chamber to which liquid supplying part 4 supplies an additional liquid is a counting chamber in which, from all counting chambers, regardless of the distance from the sucked chamber, the liquid level of the sample liquid falls to the uppermost edge of the aperture or to a predetermined liquid level faster than the other counting chambers.

As the additional liquid, a liquid that can prevent sample liquid from descending and can flow to the suction pump can be utilized. For example, diluent, washing liquid, water, physiological saline, hemolysis agent and the like can be mentioned. Of these, the diluent is preferable as an additional liquid because it can be supplied to each counting chamber through various pipings in a general particle counting apparatus such as a blood cell counting apparatus and the like, and does not influence the subsequent counting in the counting chamber. Also from this aspect, an embodiment in which the action of the liquid supplying part 4 is added to the action of the diluent supplying device attached to the particle counting apparatus, and the diluent supplying device is also made to act as the liquid supplying part 4 is preferable. The diluent may be water or may be a liquid usable for dilution of a sample for the measurement and dilution of a reagent liquid, such as physiological saline, phosphate buffer diluent and the like.

As the diluent supplying device utilizable as liquid supplying part 4, as shown in FIG. 1, (I) a diluent supplying device provided in each counting chamber, and (II) a sampling nozzle washer provided in sampling nozzle and the like are representative examples. In FIG. 1, for explanation, additional liquids 4a, 4b are supplied from both of these diluent supplying devices (I), (II). However, both or only either one of these diluent supplying devices (I), (II) may be provided.

The diluent supplying device to be provided on each counting chamber is provided on each counting chamber to dilute a sample or a sample liquid as necessary, as exemplified in FIG. 1. The diluent supplying device is an device capable of supplying diluent 4a to each counting chamber from diluent supplying source 43 as a liquid supplying source through liquid supply piping P4 and liquid supply port 42. In FIG. 1, for explanation, the diluent supplying device provided on WBC chamber 2 is shown. However, the diluent supplying device may also be provided on RBC chamber 1. By controlling the diluent supplying device, only a predetermined amount of the diluent can be supplied to the predetermined counting chamber at a predetermined time.

The sampling nozzle washer is, as shown in FIG. 1, a device that can move with sampling nozzle 5, and wash the outer surface of the sampling nozzle while allowing a liquid (e.g., diluent) to flow out and drop on the outer surface. The sampling nozzle 5 is a thin and long tube which moves to a specimen container, a necessary reagent container (not shown) and each counting chamber to perform sucking and discharging of the specimen liquid, reagent liquid, and the like. Sampling nozzle 5 is attached to the transfer mechanism so that it can move in the horizontal direction and the vertical direction. The uppermost edge of the sampling nozzle is connected to the sucking and discharging pump through the electromagnetic valve and the like. Illustration of these transfer mechanisms, piping and pump is omitted. The sampling nozzle washer has a liquid supplying source (diluent supplying source in the example of FIG. 1) 43, a liquid outlet part 41 attached to sampling nozzle 5, and liquid supply piping P5 connecting the liquid supplying source 43 and liquid outlet part 41, and washes the outer surface of the sampling nozzle 5 by allowing the liquid (e.g., diluent in the example of FIG. 1) 4b to flow out and drop on the outer surface. Therefore, by controlling the movement of the sampling nozzle 5 and the action of the sampling nozzle washer, it is possible to supply a predetermined amount of the diluent to the predetermined counting chamber at a predetermined time.

The above-mentioned diluent supplying device provided on the counting chambers and sampling nozzle washer can also act as the liquid supplying part 4 in the present invention in addition to the original action by changing the control configuration in the control part described later.

Other Embodiment of Liquid Supplying Part

As shown in FIG. 1, piping P6 is connected to a lower part of the counting chambers 1, 2 via electromagnetic valves V1, V2. Piping P6 and electromagnetic valves V1, V2 may be constituted to be able to feed various fluids into and out from each counting chamber from various pumps (not shown) by switching the electromagnetic valve, such as discharging a liquid remaining in the counting chambers 1, 2, feeding air for stirring and the like. Therefore, it may be configured such that an additional liquid can be supplied to the object counting chamber by modifying electromagnetic valves V1 and V2 and piping P6, and adding necessary electromagnetic valves and piping to form liquid supplying part 4.

Other Embodiments of Liquid Supplying Part

In the example of FIG. 1, the lowering of the liquid level of the sample liquid in the counting chamber is prevented since the liquid supplying part 4 supplies an additional liquid into the counting chamber. Such prevention of the lowering of the liquid level of the sample liquid can also be achieved by supplying the additional liquid into a flow path (i.e., piping P2 and small chamber 22) on the predetermined counting chamber (WBC chamber 2)-side than the confluence part J1 in the confluent piping shown in FIG. 1. In the confluent piping shown in FIG. 3, piping P7 from diluent supplying source 43 joins at confluence part J2 of piping P21 and supplies an additional liquid. By supplying the additional liquid into the flow path on the predetermined counting chamber side than the confluence part, sucking of the sample liquid in the predetermined counting chamber is cancelled, the sample liquid does not flow out from the aperture of the predetermined counting chamber, whereby lowering of the liquid level of the sample liquid in the predetermined counting chamber is prevented.

The supply amount and supply time of the additional liquid into the flow path may be the same as those of the additional liquid into the counting chamber explained in the example of FIG. 1.

Figure 4:
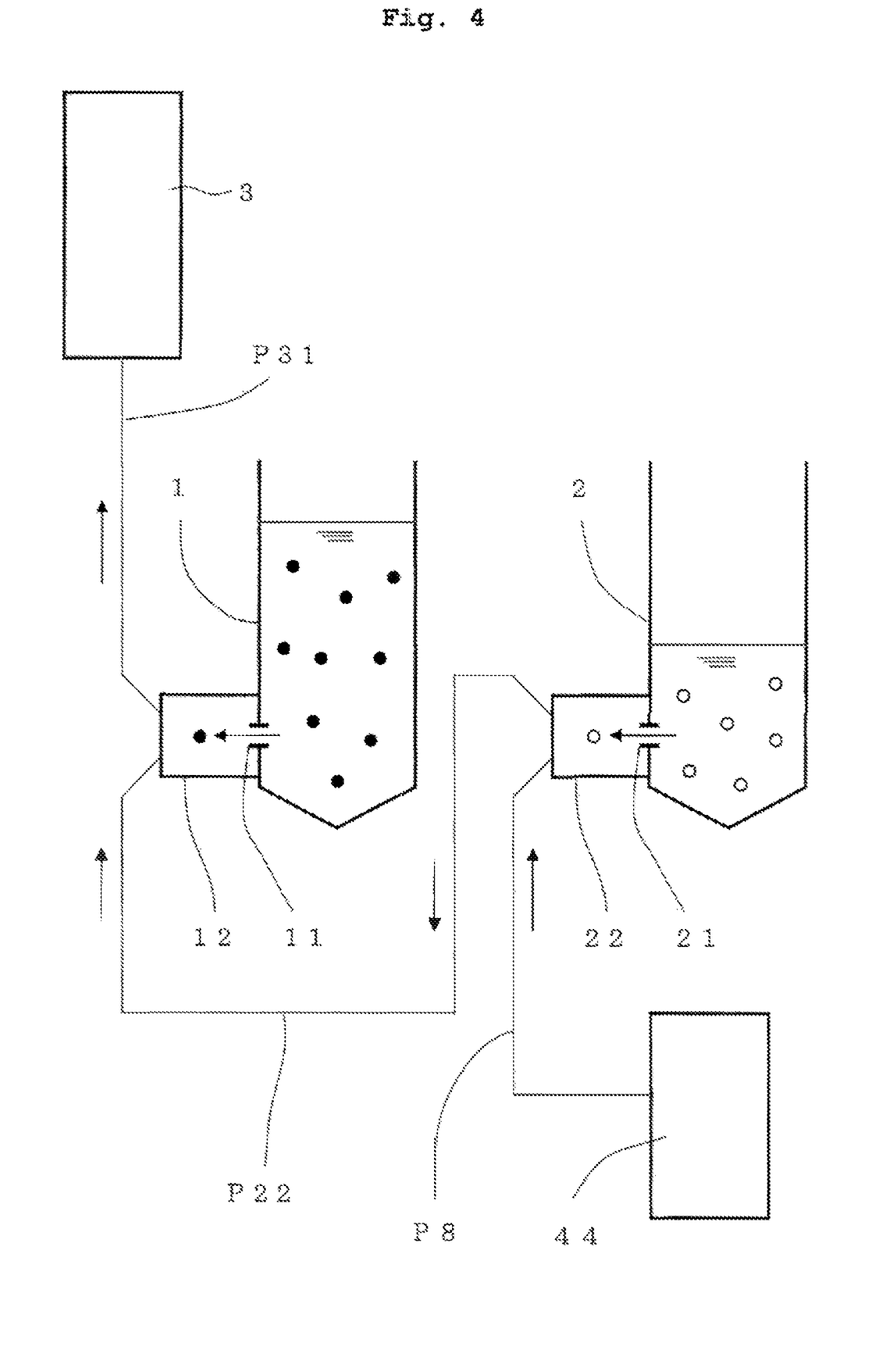
FIG. 4 is a block diagram showing another Example.

FIG. 4 is a block diagram showing another Example. In the example of this Figure, a liquid supplying part is provided but not shown. In the example of FIG. 4, a diluent supplying source 44 for rectifying is further provided, and the piping P8 connected to the diluent supplying source 44 is connected to small chamber 22 of WBC chamber 2. In the embodiment of FIG. 4, piping P8 is connected to the small chamber 22 in an inclined manner such that the flow of a diluent that flows into small chamber 22 from piping P8 advances toward the inlet of piping P22. On the other hand, piping P22 is connected to the small chamber 22 in an inclined manner such that it receives the diluent that flows into small chamber 22 from piping P8 more smoothly. The connection part of piping P8 on the inlet side of small chamber 22 is located on the lower side and the connection part of piping P8 is located on the upper side.

Due to the connection embodiment of the piping P8 and the piping P22 to the small chamber 22 and the positional relationship between the upper and lower connection parts, n effect is obtained that the flow of the additional liquid flowing into the small chamber 22 rectifies the flow of the sample liquid exiting from the aperture 21, as well as an effect is obtained that bubbles do not occur easily in small chamber 22.

Similarly, in small chamber 12 of RBC chamber 1, piping P22 is connected to the small chamber 12 in an inclined manner, piping P32 is connected to the small chamber 22 in an inclined manner and, in small chamber 12, the connection part of piping P22 on the inlet side is located on the lower side and the connection part of piping P32 on the outlet side is located on the upper side.

Due to the connection embodiment of the piping P22 and the piping P32 to the small chamber 12 and the positional relationship between the upper and lower connection parts, an effect is obtained that the flow of the liquid flowing into the small chamber 12 rectifies the flow of the sample liquid exiting from the aperture 11, as well as an effect is obtained that bubbles do not occur easily in small chamber 12.

In addition, by the piping from the diluent supplying source 44 for rectification via piping P8, small chamber 22, piping P22, small chamber 12, piping P32 to reach suction pump 3, the same amount of liquid can be supplied more reliably to small chamber 22, small chamber 12, and thus, the effect that the flow of each aperture can be more preferably rectified is obtained. When the diluent is supplied to each small chamber individually via an electromagnetic valve, time and the like are required to control the electromagnetic valve and the measurement time for one sample becomes longer. Also in this respect, the configuration of FIG. 4 is a preferable connection configuration which does not require complicated control.

It is preferable to add the embodiment shown in FIG. 4 to the examples shown in FIG. 1, FIG. 3, FIG. 5, FIG. 6. In these Figures, illustration is omitted.

Control Part

The particle counting apparatus preferably has a control part that controls the action of each part. In addition, the control part preferably further has an arithmetic part that performs arithmetic processing of particle counting based on the electric resistance method. As such control part, a computer is appropriate. The computer works with a program that controls the action of each part. The aforementioned arithmetic part is preferably configured to perform arithmetic processing for various measurements, which is included as a part of the program and includes arithmetic processing of particle counting based on the electric resistance method.

An electronic power supply, an air pressure source, an electromagnetic valve, an electric motor, and the like may be provided appropriately to operate each part in response to a command (electric signal) from the control part.

Figure 5:
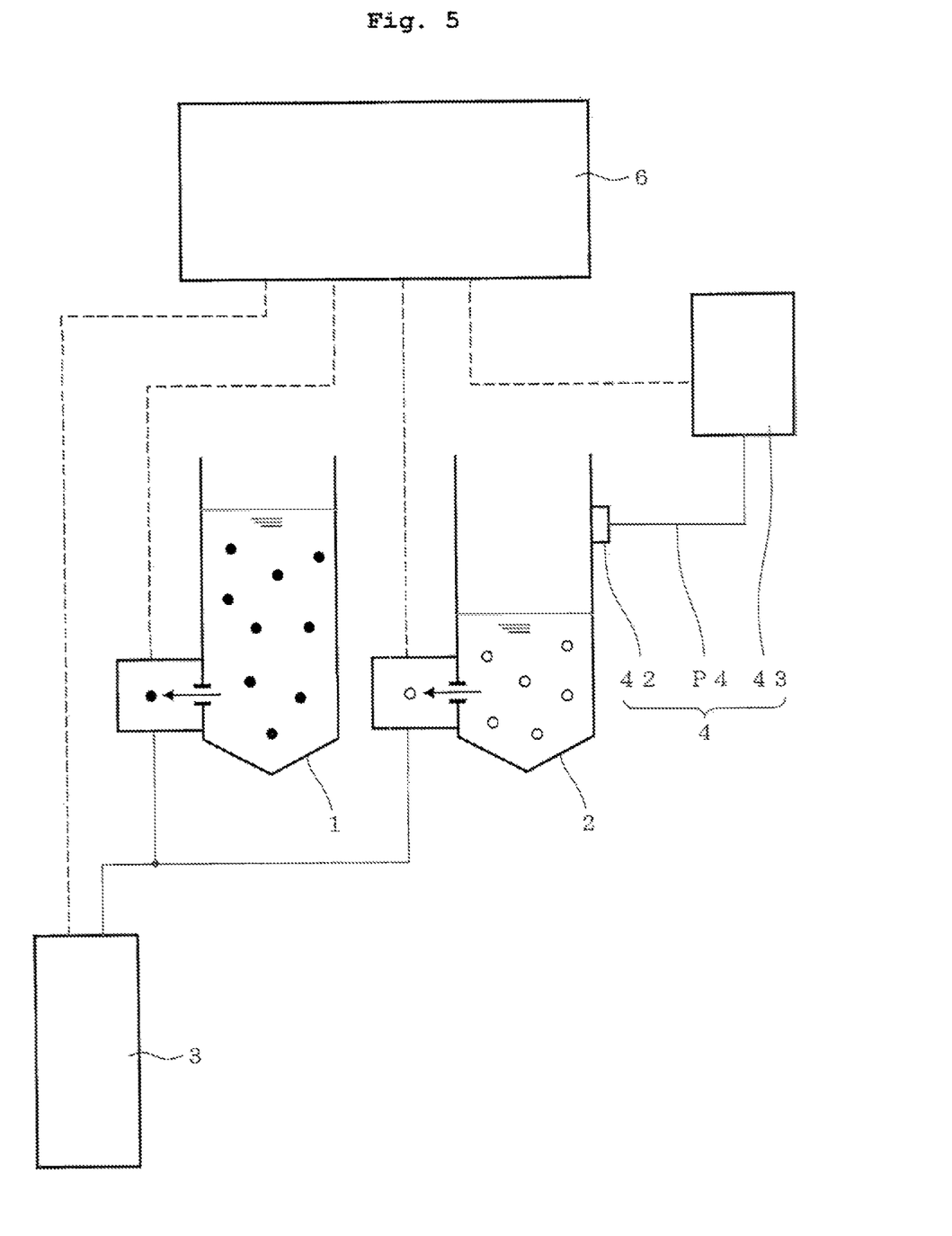
FIG. 5 is a block diagram illustrating a control part of the particle counting apparatus of the present invention. In this Figure, the connections between each main part of the particle counting apparatus and a control part are shown with dashed lines.

FIG. 5 is a block diagram showing one embodiment of the control contents of the control part. The example of this Figure shows a configuration in which control part 6 performs arithmetic processing of particle counting in RBC chamber 1 and WBC chamber 2, control of suction pump 3 for sucking the sample liquid in these chambers, control of liquid supplying part 4. In FIG. 5, as the liquid supplying part 4, the diluent supplying device provided on WBC chamber 2 is shown. The connection between each counting part and the control part 6 is indicated by a dashed line, but the actual electric wiring may be plural as necessary. Control of other action parts, such as control of sampling nozzle action and control of sampling nozzle washer and the like is omitted.

The control part 6 starts particle counting based on the electric resistance method by controlling suction pump 3, sucking the sample liquid in RBC chamber 1 and WBC chamber 2, and simultaneously activating the constant voltage electronic power supply (not shown) to apply constant voltage to each electrode pair (not shown) of RBC chamber 1 and WBC chamber 2. The voltage pulse generated in each electrode pair due to the passage of blood cell is processed by the arithmetic part included in the control part 6, and the counting result is calculated. While the time of completion of the counting in WBC chamber 2 is roughly determined beforehand, the completion time may be determined based on the result of the processing by the operation part. When the counting in WBC chamber 2 is completed, the control part 6 controls the pump (not shown) of the diluent supplying source 43, supplies a diluent to the WBC chamber 2 via the piping P4, the liquid supply port 42, and prevents lowering of the liquid level of the sample liquid. The control part 6 continues counting in the RBC chamber 1 and, for example, when the counting is completed, discontinues the action of the suction pump 3, application of voltage to the electrode pair of the RBC chamber 1, and the action of the pump in the diluent supplying source 43, and completes the action relating to counting.

The control part 6 may be configured to determine whether to extend counting in each counting chamber based on the counting result calculated by the arithmetic part, extend the action of the suction pump based on the determination result, extend the counting of the counting chamber determined to be extended and calculate the counting result. As such control configuration, for example, control part 6 has, for example, a configuration provided with a storage part, a determination part and an extension instructing part. The storage part stores determination conditions previously determined for each counting chamber. The determination part compares the counting result of each counting chamber calculated by the arithmetic part with the determination condition (e.g., normal range of the number of specific blood cells, etc.) stored in the storage part. When the determination part determines that the counting result in a certain counting chamber is out of the determination condition, it informs the extension instructing part that the counting in the counting chamber should be extended. The determination part may also serve as an extension instructing part. The extension instructing part instructs the control part 6 to extend the counting. The control part 6 causes the suction pump to extend the action to suck the sample liquid through the aperture. In addition, the control part 6 causes the operation part to process the pulse voltage sent from the counting chamber determined to be extended, and to calculate the further counting result of the counting chamber.

More Specific Action Example of Particle Counting Apparatus

More specific action example of a particle counting apparatus (blood cell counting apparatus) having RBC chamber 1 and WBC chamber 2 exemplified in FIG. 1 is shown. The action of each part is controlled by a control part.

As mentioned above, the counting chamber in which the counting is completed last is RBC chamber 1, and the counting chamber to be supplied with the additional liquid is WBC chamber 2. In this example, all these counting chambers may be containers with a cylindrical shape and the same inner diameter or different inner diameters.

In the particle counting apparatus, a specimen container (not shown) containing a sample liquid such as whole blood and the like is set. In addition, the particle counting apparatus is provided with the sampling nozzle 5 shown in FIG. 1 as a preferable embodiment.

In a specific action example of the particle counting apparatus, a sampling nozzle first moves to a specimen container and sucks a specimen liquid (whole blood) in the specimen container. Thereafter, the outer surface of the sampling nozzle may be washed in a wash chamber (not shown) with the diluent 4b discharged from the sampling nozzle washer (described later).

Then, the sampling nozzle moves to the WBC chamber 2 and dispenses a predetermined amount of the sucked specimen into the WBC chamber 2.

As shown in FIG. 1, a liquid supply port 42 is provided on the side surface of WBC chamber 2, and the diluent supplying source 43 is connected to the liquid supply port via liquid supply piping P4. The diluent supplying source 43 may be contained in the particle counting apparatus. A predetermined amount of the diluent is injected into the chamber 2 from the liquid supply port 42 and stirred to dilute the specimen at a predetermined magnification.

A part of the specimen liquid in which the specimen is diluted in the WBC chamber 2 is transferred to the RBC chamber 1 by a predetermined amount.

Similar to WBC chamber 2, by a liquid supply port (not shown) provided also in the RBC chamber 1 and the diluent supplying source (not shown) connected thereto, a predetermined amount of the dilution liquid is injected into RBC chamber 1 and stirred, and the sample liquid is further diluted to a predetermined magnification. As a result of this dilution, the liquid level of the sample liquid M1 in the RBC chamber 1 becomes higher than the liquid level of the sample liquid M2 in the WBC chamber 2.

A hemoglobin hemolysis reagent is injected into WBC chamber 2, stirred, and the sample liquid is subjected to a hemolysis treatment.

The suction pump 3 is activated to simultaneously suck the sample liquids of RBC chamber 1 and the WBC chamber 2, and in these chambers, blood cell counting based on the electric resistance method is simultaneously started. The pulse voltage obtained when red blood cell (may include platelets) X1, white blood cell X2 pass through apertures 11, 21 of RBC chamber 1 and WBC chamber 2, respectively, is processed in the below-mentioned control part, and the numbers of red blood cells, white blood cells, and further, number per volume of each blood cell are calculated. Red blood cells and platelets can be clearly distinguished from large differences in their volumes.

When the counting in the WBC chamber 2 is completed, the liquid level of the sample liquid has dropped close to the aperture. On the other hand, in RBC chamber 1, counting has not been completed yet. From this point until the time point before the liquid level of the sample liquid of the WBC chamber 2 reaches the uppermost edge of the aperture or a predetermined liquid level, the liquid supplying part 4 is activated to supply the additional liquid to the WBC chamber 2 to prevent the sample liquid from descending in the WBC chamber 2.

Thereafter, suction pump 3 simultaneously sucks the sample liquid M1 of RBC chamber 1 and [mixture of remainder of sample liquid M2 and additional liquid] in WBC chamber 2, and the counting in RBC chamber 1 is completed without problems such as air being sucked in WBC chamber 2.

When the particle counting apparatus is a blood cell counting apparatus, the amount of the sample fluid before dilution and supplied to the WBC chamber is not particularly limited and is, for example, about several μL to several hundreds μL (L represents liter). As for the dilution factor, the known art can be referred to. In addition, the amount of the sample liquid before dilution and supplied to RBC chamber is not particularly limited, either, and is several tens to several tens of thousands times the amount of sample liquid before dilution and supplied to the WBC chamber. As for the dilution factor, the known art can be referred to. The time required for counting in the WBC chamber is not particularly limited and is several seconds to several tens of seconds. The counting time in the RBC chamber is usually several seconds to several tens of seconds longer than the counting time of the WBC chamber.

Various measurement chambers such as a counting chamber based on flow cytometry, an immunoassay chamber and the like may be provided in the particle counting apparatus. It is preferable that the control part be configured to control the operation of each part so that various measurements in those chambers can be performed and the operation part included in the control part are configured to perform arithmetic processing for those measurements.

The particles to be counted by the particle counting apparatus may be various particles such as particles made of inorganic materials such as ceramic particles and the like, particles made of resin materials such as polystyrene, and the like as well as blood cells such as red blood cell, white blood cell and the like.

Figure 6:
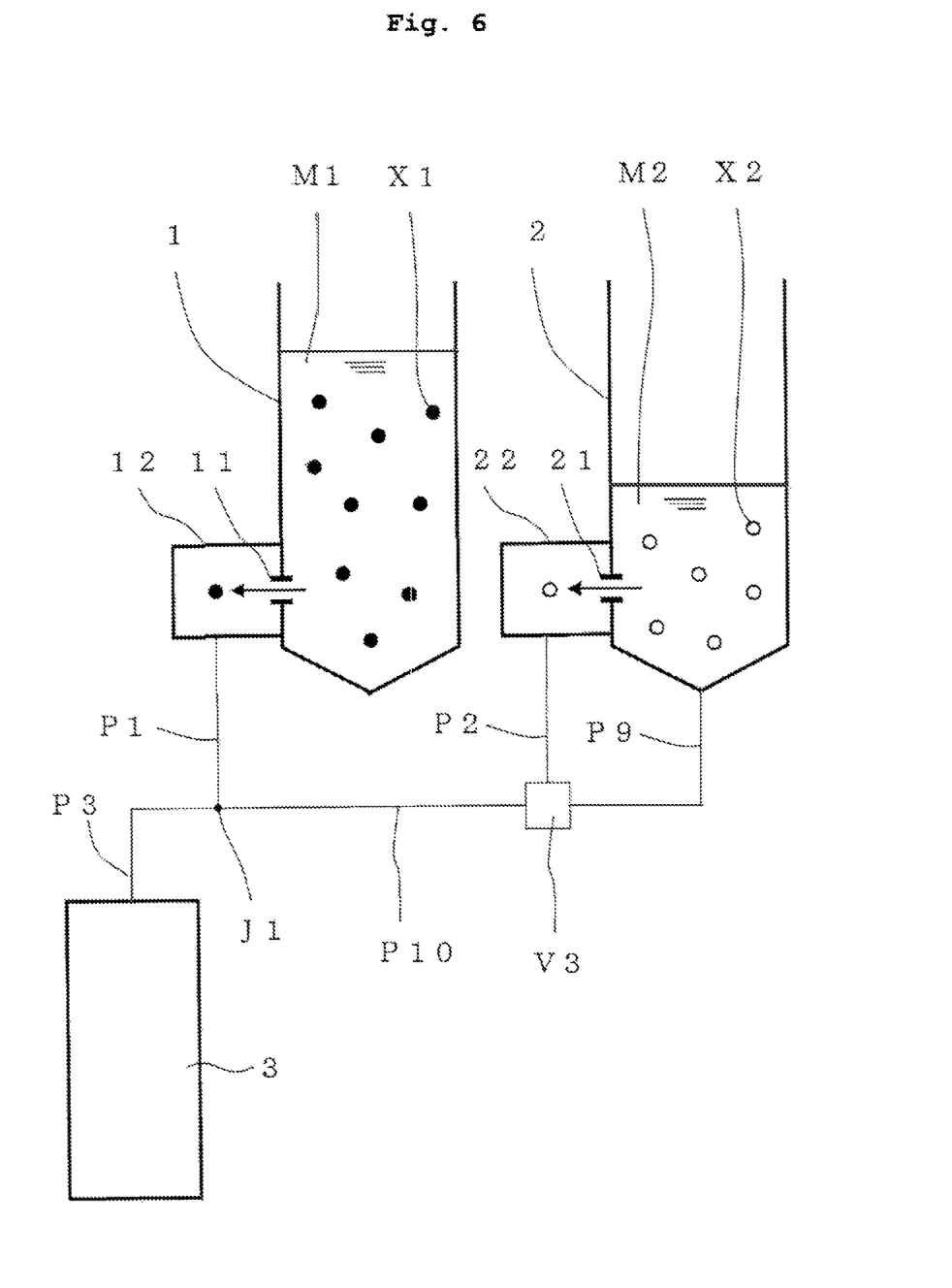
FIG. 6 is a block diagram showing other embodiment of the particle counting apparatus of the present invention. In this Figure, the connection between the counting chambers and the suction pump, and a liquid supplying part and other piping are omitted.

In the particle counting apparatus, an embodiment utilizing a suction pump to discharge the sample liquid remaining in the counting chamber is proposed as shown in FIG. 6.

As shown in FIG. 6, in this embodiment, suction pump 3 simultaneously performs sucking for discharging the sample liquid left in the other counting chamber 2 in which the counting has been completed, while sucking the sample liquid in the counting chamber 1 under counting. The counting chamber 2 shown in FIG. 6 may be a chamber for waste liquid or other counting chamber without the aperture. In the example of FIG. 6, piping P9 and electromagnetic valve V3 for switching the flow path are sequentially connected to the lower part of the counting chamber 2, and piping P10 joins piping P3 at confluence part J1. The electromagnetic valve V3 can switch between piping P2 and piping P9 and connect same to piping P10. The suction pump 3 can switch and perform the next action by this switchable confluent piping.

(1) Action to suck the sample liquids of counting chambers 1, 2 through each aperture and pipings P1, P2, P10, P3.

(2) Action to suck the liquid remaining in counting chamber 2 after completion of counting and other chambers (chamber for waste liquid, other counting chamber without an aperture and the like) through pipings P9, P10, P3 while sucking the sample liquid of counting chamber 1 via aperture and pipings P1, P3.

Such switchable confluent piping makes it possible to shorten the total action time necessary for the analysis of one sample. In addition, by switching the flow path, air is not drawn from the aperture of counting chamber 2.

INDUSTRIAL APPLICABILITY

The present invention is useful for particle counting apparatuses having a plurality of counting chambers for performing particle counting based on the electric resistance method. While it has a configuration in which the sample liquid of each counting chamber is sucked by a common suction pump, it enables particle counting to be preferably completed in any counting chamber.

This application is based on a patent application No. 2016-243852 filed in Japan (filing date: Dec. 15, 2016), the contents of which are incorporated in full herein.

EXPLANATION OF CHARACTERS 1, 2 counting chamber
3 suction pump
4 liquid supplying part
5 sampling nozzle
11, 21 aperture
M1, M2 sample liquid
X1, X2 particle

The invention claimed is:

1. A particle counting apparatus for counting particles in a sample liquid, comprising
    a plurality of counting chambers each provided with an aperture and a pair of electrodes for counting particles based on the electric resistance method,
    a suction pump, and
    a liquid supplying part for supplying a liquid to one or more predetermined counting chambers,
wherein
    the aperture of each of the plurality of counting chambers has an outside opening connected to the suction pump through a confluent piping, and
    the liquid supplying part supplies a liquid to said one or more predetermined counting chambers or to a flow path on the predetermined counting chamber side than a confluent part in the confluent piping, after completion of counting in said one or more predetermined counting chambers, such that a liquid level of the sample liquid in said one or more predetermined counting chambers would not descend to the aperture or to a predetermined liquid level above the aperture.

2. The particle counting apparatus according to claim 1, wherein
    the plurality of counting chambers are cylindrically-shaped containers with a same inner diameter, and
    a liquid level of the sample liquid in a counting chamber in which the counting is completed last is higher than the liquid level of the sample liquid in the one or more predetermined counting chambers at the time point when the sample liquid has been injected into each of the plurality of counting chambers.

3. The particle counting apparatus according to claim 1, wherein
    the plurality of counting chambers comprise a red blood cell counting chamber and a white blood cell counting chamber,
    a counting chamber in which the counting is completed last is the red blood cell counting chamber, and
    the one or more predetermined counting chambers are white blood cell counting chambers.

4. The particle counting apparatus according to claim 1, wherein
    the liquid supplied by the liquid supplying part is a diluent, and
    the liquid supplying part comprises one or both of a diluent supplying device of the following (I) and a sampling-nozzle washer of the following (II):

(I) a diluent supplying device comprising a diluent supplying source, a diluent supply port provided in the one or more predetermined counting chambers, and a diluent supplying piping connecting the diluent supplying source and the diluent supply port (II) a sampling nozzle washer comprising a diluent supplying source, a diluent outlet part accompanying a sampling nozzle provided in the particle counting apparatus, and a diluent supplying piping connecting the diluent supplying source and the diluent outlet part, wherein an outer surface of the sampling nozzle is washed while allowing the diluent to flow out on and drop from the outer surface.

* * * * *